United States Patent [19]

Jacobson

[11] 4,062,903

[45] Dec. 13, 1977

[54] PROCESS FOR ISOMERIZING ALKYLAROMATICS

[75] Inventor: Robert L. Jacobson, Pinole, Calif.

[73] Assignee: Chevron Research Company, San Francisco, Calif.

[21] Appl. No.: 726,359

[22] Filed: Sept. 24, 1976

[51] Int. Cl.$^2$ ............................................. C07C 15/08
[52] U.S. Cl. ............................ 260/668 A; 260/674 H
[58] Field of Search ........... 260/668 A, 668 R, 674 H

[56] References Cited

U.S. PATENT DOCUMENTS

| Re. 25,753 | 4/1965 | Holm | 260/674 H |
|---|---|---|---|
| 3,078,318 | 2/1963 | Berger | 260/668 A |
| 3,642,925 | 2/1972 | Rausch | 260/668 A |
| 3,766,287 | 10/1973 | Stenmark et al. | 260/668 A |

Primary Examiner—Veronica O'Keefe
Attorney, Agent, or Firm—D. A. Newell, R. H. Davis, W. D. Reese

[57] ABSTRACT

A process is disclosed for producing a selected $C_8$ alkylaromatic isomer from a feedstock containing a less than equilibrium concentration of the selected isomer and a low $C_8$ naphthenes concentration, in which the feedstock is first contacted with a platinum-halogen catalyst at low temperature isomerization conditions to form an intermediate reaction mixture containing a substantial amount of $C_8$ naphthenes and a partially isomerized mixture of $C_8$ alkylaromatics; the intermediate mixture is then contacted with another platinum-halogen catalyst at higher temperature dehydrogenation conditions to form a final product mixture with a very low naphthenes content and a substantially equilibrium concentration of the selected isomer; and the selected xylene isomer is recovered from the final product mixture.

3 Claims, 3 Drawing Figures

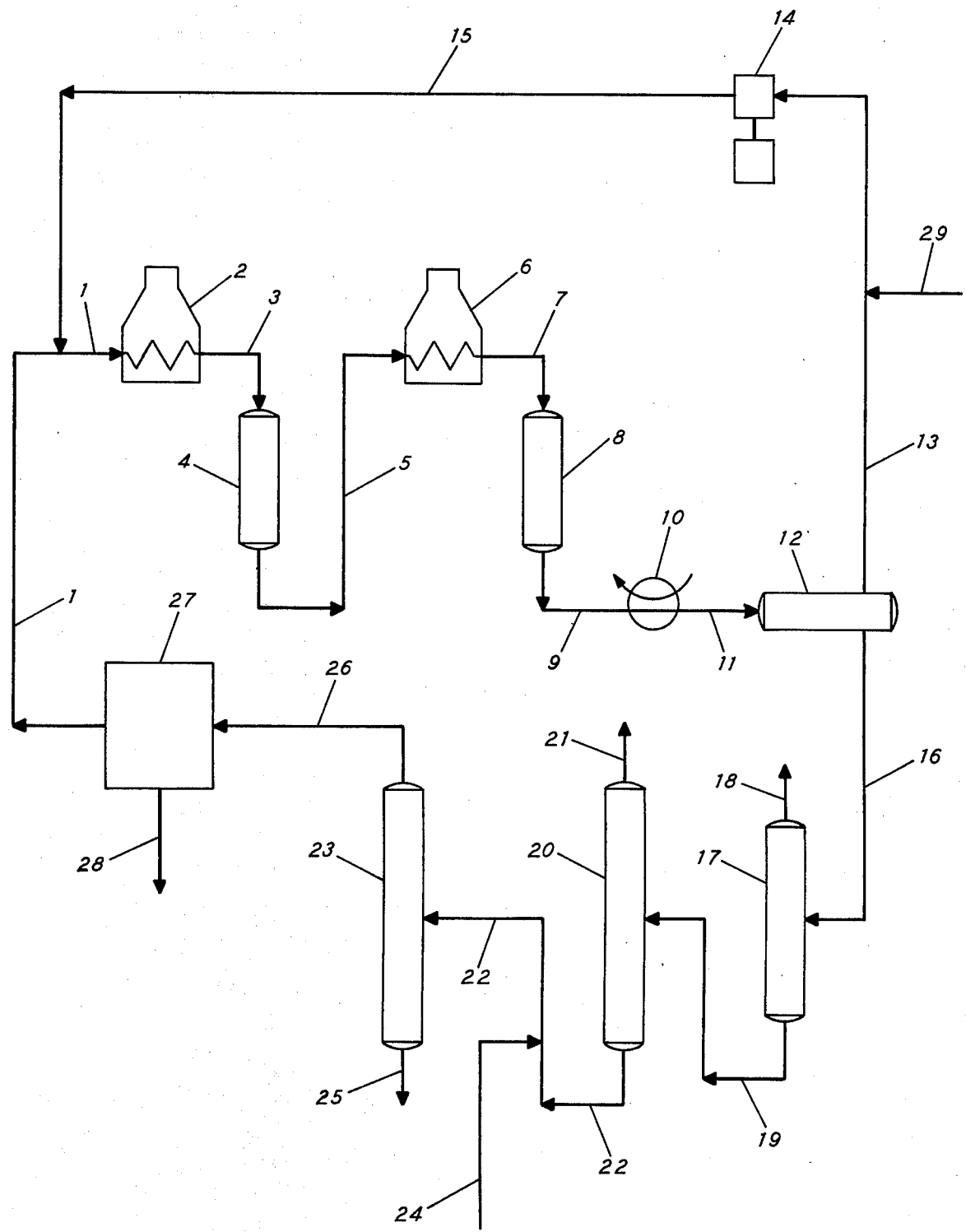

PROCESS FOR ISOMERIZING ALKYLAROMATICS

BACKGROUND OF THE INVENTION

The present invention relates to a process for isomerizing $C_8$ alkylaromatic hydrocarbons.

Processes for producing particular xylene isomers from $C_8$ alkylaromatic feedstocks are well known. Typically, a selected xylene isomer is received from a petroleum fraction, such as reformate, rich in $C_8$ alkylaromatics, as by fractionation, crystallization, or molecular sieve-type separation. Paraxylene is usually the isomer sought to be recovered, orthoxylene is occasionally the selected isomer, and metaxylene and ethylbenzene are rarely desired as products. After the selected xylene isomer has been removed from the petroleum fraction, the $C_8$ alkylaromatic residue is often treated in a $C_8$ alkylaromatic isomerization operation in order to form additional amounts of the selected xylene isomer. The newly formed amounts of the xylene isomer are then recovered from the isomerate by the same separation operation used with the original petroleum fraction. Usually, the isomerization operation involves primarily conversion of metaxylene, and sometimes ethylbenzene, to paraxylene. Ethylbenzene has been found to be relatively difficult to convert to xylenes, as compared to the relatively easy conversion of one xylene isomer to another. The concentration of ethylbenzene in an isomerization-separation system tends to build up undesirably in the processing streams, as the selected xylene isomer is removed and the residue is recycled to isomerization.

Various isomerization catalysts and flow schemes have been suggested by the art in attempting to provide efficient isomerization and recovery systems for producing a selected xylene isomer. For example, U.S. Pat. No. Re. 25,753 discloses a two-stage process for isomerizing xylenes. In the first stage, a xylene, or non-equilibrium mixture of xylenes, is contacted with a hydrogenation-dehydrogenation catalyst under hydrogenation conditions to convert a large proportion (10–35%) of the xylenes in the feed to naphthenes. In the second stage, the naphthenes produced in the first stage are contacted with a hydrogenation-dehydrogenation catalyst under dehydrogenation conditions to reconvert the naphthenes to xylenes, and simultaneously to isomerize the xylenes during dehydrogenation. One catalyst described as useful in the process is platinum on alumina or silica-alumina.

U.S. Pat. No. 3,078,318 describes the isomerization of a xylene or non-equilibrium mixture of xylenes with a platinum-halogen-alumina catalyst in a hydrogen atmosphere at 700°–1100° F and 1–1500 atmospheres pressure. A selected xylene isomer is separated from the isomerization reactor effluent and the residue from the isomer separation step is recycled to the isomerization step.

U.S. Pat. No. 3,381,048 describes a process for isomerization of a xylene isomer or non-equilibrium mixture of xylene isomers using a platinum-halogen-alumina catalyst. In the process, the water content of the hydrocarbon feed to the isomerization reactor is kept at 20–200 parts per million.

U.S. Pat. No. 3,538,173 describes a process for isomerizing xylenes in which ethylbenzene in a $C_8$ alkylaromatic-containing stream is isomerized to xylenes by controlling the $C_8$ naphthenes content in the feed introduced into the isomerization reactor to keep the $C_8$ naphthenes content of the feed at 2–9 weight percent of the $C_8$ alkylaromatic content of the feed. A platinum-halogen-alumina catalyst is employed in the isomerization reactor at a temperature of 700°–840° F and a pressure of 3–20 atmospheres.

U.S. Pat. No. 3,553,276 describes a process for isomerizing xylenes in which, during recovery of a selected xylene isomer from the reactor effluent, loss of $C_8$ naphthenes from the system is minimized by maintaining a high concentration of diluent toluene in the effluent from the isomerization reactor. This is accomplished by introducing large amounts of diluent toluene into the isomerization reactor in the feed. A platinum-halogen-alumina catalyst is used in the isomerization step at a temperature of 32°–1290° F and a pressure of 1–100 atmospheres, or more.

U.S. Pat. No. 3,879,484 describes a process for isomerizing $C_8$ alkylaromatic hydrocarbons such as xylenes by contacting the $C_8$ alkylaromatic with a platinum-rhenium-halogen-alumina catalyst at a temperature of 32°–1112° F and a pressure of 1–100 atmospheres.

SUMMARY OF THE INVENTION

In an embodiment, the present invention relates to a process for producing a first $C_8$ alkylaromatic hydrocarbon isomer from a feedstock including a substantially greater than equilibrium concentration of a second $C_8$ alkylaromatic hydrocarbon isomer, a substantially less than equilibrium concentration of the first isomer, and a weight ratio of $C_8$ naphthenes to $C_8$ alkylaromatics of less than 1:50 by steps comprising: forming an intermediate hydrocarbon reaction mixture having a weight ratio of $C_8$ naphthenes to $C_8$ alkylaromatics of more than 1:50 and less than 1:10 by contacting hydrogen and the feedstock with a first catalyst comprising 0.1–3 weight percent platinum and 0.5–5 weight percent chloride on a porous solid carrier at isomerization conditions including an isomerization temperature of 750°–900° F and an isomerization hydrogen pressure of 100–250 psi; forming a final product mixture including a substantially equilibrium concentration of the first isomer and a weight ratio of $C_8$ naphthenes to $C_8$ alkylaromatics of less than 1:50 by contacting the intermediate reaction mixture and hydrogen with a second catalyst comprising 0.1–3 weight percent platinum and 0.5–5 weight percent chloride on a porous solid carrier at dehydrogenation conditions including a temperature at least 25° F higher than the isomerization temperature and at a hydrogen pressure not higher than the isomerization pressure; and recovering the first isomer from the final product mixture.

I have found that by employing a platinum-rhenium-chloride catalyst in a two-stage conversion system, in which isomerization and a controlled amount of hydrogenation are carried out in the first stage, while dehydrogenation of naphthenes is carried out in the second stage, excellent isomerization of $C_8$ alkylaromatics, and particularly of ethylbenzene to xylenes, can be obtained without any substantial loss of hydrogen from the system in naphthenes during subsequent operations to separate and recover the desired $C_8$ alkylaromatic isomer. Moreover, according to the invention, diluent and by-product toluene can be removed from the system without resorting to the use of undesirably high ethylbenzene and toluene recycle rates in the system to control loss of hydrogen and $C_8$ naphthenes.

DESCRIPTION OF THE DRAWINGS

The attached drawing is a schematic representation of one preferred embodiment of the present invention.

Referring to the drawing, a hydrocarbon feed stream containing a non-equilibrium of $C_8$ alkylaromatic and having a $C_8$ naphthenes/$C_8$ alkylaromatics weight ratio below 1:50; previously derived in the system as described below, is mixed with hydrogen from a source described below in conduit 1, and the hydrogen-hydrocarbon mixture is passed through a heater 2 to raise the temperature of the mixture to a selected level in the range from 750°–850° F. The resulting heated mixture is passed through conduit 3 into isomerization-hydrogenation reactor 4, in which the mixture is contacted with a catalyst containing platinum, rhenium and chloride on an alumina carrier at isomerization conditions including a temperature of 750° F to 850° F. An intermediate hydrocarbon reaction mixture including a substantially equilibrium mixture of $C_8$ alkylaromatics and a $C_8$ naphthenes/$C_8$ alkylaromatics weight ratio of more than 1:50 and less than 1:10 is withdrawn from reactor 4 in admixture with hydrogen and is passed through conduit 5 into heater 6, wherein the intermediate reaction mixture and hydrogen are further heated to a temperature at least 25° F higher than the isomerization temperature. The heated hydrogen-hydrocarbon mixture is then passed through conduit 7 into dehydrogenation reaction 8, and is contacted therein with a catalyst containing platinum, rhenium and chloride on an alumina carrier. The pressure maintained in reactor 8 is substantially the same as the pressure maintained in reactor 4, except for a small pressure drop due to fluids handling. A final hydrocarbon product mixture, including a substantially equilibrium mixture of $C_8$ alkylaromatic hydrocarbons and a $C_8$ naphthenes/$C_8$ alkylaromatics weight ratio below 1:50, is removed from reactor 8 along with hydrogen, and the hydrogen and the hydrocarbons are passed through conduit 9 into cooler 10. The resulting cooled, liquid final product mixture and gaseous hydrogen are then passed through conduit 11 into vapor-liquid separator 12. Hydrogen is withdrawn overhead from separator 12 and is passed through conduit 13, compressor 14 and conduit 15 into conduit 1 for further use in the system as described above. Liquid final hydrocarbon product mixture is withdrawn from separator 12 and passed through conduit 16 into fractionator 17, wherein the liquid product mixture is stabilized. Light gases such as $C_1$–$C_4$ hydrocarbons are removed overhead from fractionator 17 through conduit 18 and are withdrawn from the system. Hydrocarbons boiling above $C_4$ are removed as bottoms from fractionator 17 and are passed through conduit 19 to fractionator 20. In fractionator 20, toluene and lower boiling hydrocarbons are separated and removed overhead through conduit 21 and withdrawn from the system. $C_8$ alkylaromatic hydrocarbons and higher boiling hydrocarbons are removed from fractionator 20 as bottoms through conduit 22 and are passed through into fractionator 23. Fresh feed $C_8$ alkylaromatics are introduced into conduit 22 from conduit 24. Hydrocarbons boiling higher than $C_8$ alkylaromatics are removed from fractionator 23 as bottoms and are withdrawn from the system through conduit 25. A $C_8$ alkylaromatic fraction is recovered overhead from fractionator 23 through conduit 26, and is passed into a paraxylene separation zone 27, wherein paraxylene is separated from the $C_8$ alkylaromatic mixture using a separation techique of known type. In separation zone 27, paraxylene is removed from the $C_8$ alkylaromatic fraction withdrawn from separation zone 27 as the product of the process through conduit 28. The nonequilibrium residue or raffinate of $C_8$ alkylaromatic hydrocarbons left behind after separation of the paraxylene product is then removed from separation zone 27 and passed into conduit 1 for isomerization treatment, as described above. Make up hydrogen is added to the system, as needed, through conduit 29, which leads into conduit 13.

Various elements employed in the embodiment depicted in the drawing, such as heating, cooling, reboiling, refluxing and control means, are not shown in the drawing or discussed in the foregoing, as their placement and operation will be obvious to those skilled in the art.

DETAILED DESCRIPTION OF THE INVENTION

The feedstocks which are employed in the process are those containing $C_8$ alkylaromatic hydrocarbons, including a greater than equilibrium concentration of an unwanted $C_8$ alkylaromatic, e.g., of ethylbenzene with respect to a desired $C_8$ alkylaromatic, e.g., paraxylene. The $C_8$ alkylaromatics may be present in the feedstocks in admixture with other hydrocarbons such as benzene, toluene, aliphatics, $C_9+$ alkylaromatics, etc. Suitable feedstocks are those having a substantially lower than equilibrium concentration of the particular $C_8$ alkylaromatic isomer which is the selected product of the process. Suitable feedstocks may be obtained from the same sources as are the charge stocks employed in conventional, commercial $C_8$ alkylaromatic isomerization operations, with one preferred source being the residual $C_8$ alkylaromatic hydrocarbons remaining after separation of a selected xylene isomer product in conventional separation operations. For example, when the selected, xylene isomer product is paraxylene, the paraxylene-depleted raffinate $C_8$ alkylaromatic fraction formed in a crystallization separation system or in a molecular sieve separation system is a suitable feedstock for use in the present process if the ethyl benzene and $C_8$ naphthenes content are suitable.

$C_8$ naphthenes are not present in suitable feedstocks in concentrations greater than those sufficient to provide a $C_8$ naphthene/$C_8$ alkylaromatic weight ratio above 1:50. Preferably, the $C_8$ naphthenes/$C_8$ alkylaromatics weight ratio of the feed is less than 1:100. Suitable feedstocks may include high ethylbenzene concentrations, since the present process is particularly adapted for use in conversion of an ethylbenzene-rich feed to provide a selected xylene isomer. Preferably, the feed contains an amount of ethylbenzene sufficient to provide a greater than equilibrium concentration of ethylbenzene with respect to the total $C_8$ alkyl aromatics concentration of the feedstock.

The feedstock is preferably dried, as by distillation drying or molecular sieve drying, so that the feed is substantially water-free when contacted with the isomerization catalysts. Thus, the water content of the feed is preferably kept below 10 ppm, and a feedstock containing less than 1 ppm water is particularly preferred.

The present process provides high yields of a selected $C_8$ alkylaromatic isomer with increased isomerization selectivity while preventing loss of hydrogen and $C_8$ naphthenes during separation and recovery product isomer. The selected isomer is preferably paraxylene, although orthoxylene, metaxylene, and in some cases, ethylbenzene, can be provided in a manner substantially the same as that used to provide paraxylene by alternatively or additionally using slightly different separation and recovery techniques which are well known to those skilled in the art. It will be appreciated that feedstocks which are to be processed according to the invention must have a substantially less than equilibrium concentration of the selected product isomer with respect to the total $C_8$ alkylaromatic content of the feedstock in order to provide an incentive for isomerization according to the present process.

In the first step of the present process, the feedstock and hydrogen are contacted with a catalyst comprising platinum and chloride on a porous carrier. A catalyst having essentially the same composition is used in the second stage of the process, more fully described below. The catalyst employed in the process includes 0.1 to 3 weight percent platinum, and preferably includes 0.1 to 1 weight percent platinum. The porous solid carrier may be a refractory inorganic oxide, or mixture of inorganic oxides, with alumina being a preferred carrier. The catalyst preferably includes 0.1-3 weight percent rhenium, with 0.1-1 weight percent rhenium being especially preferred. The platinum and rhenium components of the catalyst may be combined with the carrier according to any known method, such as aqueous impregnation followed by drying and calcination.

An important component of the catalyst used in the first and second stages of the present process is a chloride component. Chloride is present in the catalyst in an amount between 1 weight percent and 5 weight percent of the catalyst. I have found that, when using the preferred catalyst including platinum, rhenium and chloride on an alumina carrier, maintaining the chloride content of the catalyst between 1.25 weight percent and 2.0 weight percent of the catalyst gives particularly good results in the present process. This range of chloride content can be maintained during the isomerization step by drying the hydrocarbon feedstock to be processed in the isomerization step to a very low water content, i.e., below 10 ppm, and by adding 15 ppm to 100 ppm of chloride as, e.g., and organic chloride compound such as carbon tetrachloride, to the feedstock before it is contacted with the catalyst in the first step.

The first step of the process is carried out by contacting the feedstock with the catalyst under isomerization conditions sufficient to form an intermediate reaction mixture having a weight ratio of $C_8$ naphthenes to $C_8$ alkylaromatics of 1:50 to 1:10, preferably 1:14. According to the invention, the isomerization conditions employed are selected to provide not only substantial isomerization of the $C_8$ alkylaromatics, but also to provide an essential, controlled amount of hydrogenation of $C_8$ alkylaromatics to form $C_8$ naphthenes. By combining the isomerization reaction and hydrogenation reaction in the first step, it is possible to obtain excellent conversion of ethylbenzenes to xylenes, while avoiding the necessity for including naphthenes in the feedstock in order to provide ethylbenzene conversion. The controlled amount of hydrogenation which takes place in the first step of the process permits ethylbenzene to be converted to xylenes without the loss of $C_8$ naphthenes and hydrogen from the system during subsequent separation of the selected xylene isomer, as further described below. In prior art isomerization-separation systems, the use of undesirable, high naphthenes and diluent hydrocarbon levels in the feed to the isomerization operation has been required in order to avoid such hydrogen and $C_8$ hydrocarbon losses.

Isomerization conditions employed in the first stage of the process include an isomerization temperature in the range between 750° F and 900° F, preferably between 775° F and 825° F. The isomerization hydrogen pressure in the first step is maintained between 100 psia and 250 psia hydrogen. A hydrogen/hydrocarbon molar ratio of about 2 to 15 is employed. The first step may be performed in a batch type or continuous type operation. Preferably, a continuous type operation is used, employing a liquid hourly space velocity of about 0.5 to 10. Any suitable, conventional reaction vessel may be utilized in carrying out the first processing step. Furthermore, the first processing step may be carried out in more than one reaction vessel connected in series or in parallel.

The intermediate reaction mixture which results from the first step of the process includes a substantially equilibrium concentration of the selected product isomer and also includes a $C_8$ naphthenes/$C_8$ alkylaromatics weight ratio of more than 1:50 and less than 1:10, preferably 1:14. A weight ratio betwee 1:33 and 1:20 is particularly preferred.

In prior art it has been the practice to separate a $C_8$ alkylaromatics-rich fraction from the product mixture recovered from an isomerization operation and then to recover a selected xylene isomer from the $C_8$ alkylaromatics-rich fraction. In cases using such a scheme, when the product mixture has included a substantial amount of naphthenes, it has been necessary either to withdraw naphthenes from the system along with diluent hydrocarbons such as toluene or else to leave excessive amounts of diluents such as toluene in the system as part of the $C_8$ alkylaromatic-rich fraction. Withdrawing substantial amounts of naphthenes from the system along with by-product and diluent toluene has resulted in the loss of substantial amounts of hydrogen from the processing system and has lowered the overall yield of the selected $C_8$ alkylaromatic isomer product. The present process obviates the necessity for either leaving large amounts of undesirable toluene diluent in the $C_8$ alkylaromatics-rich fraction or else losing large amounts of hydrogen and $C_8$ alkylaromatic hydrocarbons during separation of the $C_8$ alkylaromatics-rich fraction from other hydrocarbons.

According to the invention, the intermediate reaction mixture formed in the first step is subjected to a second treatment with an isomerization catalyst, such as the same type used in the first step, but at reaction conditions which dehydrogenate result in dehydrogenation of naphthenes formed in the first step to form $C_8$ alkylaromatic hydrocarbons. Thus, hydrogen and $C_8$ alkylaromatics are formed in the second step of the process when $C_8$ naphthenes are dehydrogenated, so that loss of hydrogen from the system as a component of $C_8$ naphthenes is minimized and loss of $C_8$ alkylaromatics as a component of naphthenes is likewise minimized.

The dehydrogenation step of the process may utilize the same type catalyst employed in the first, isomerization step. The second step is carried out by contacting the intermediate reaction mixture with the dehydrogenation catalyst at dehydrogenation conditions sufficient to form a final hydrocarbon product mixture having a substantialy equilibrium concentration of the selected $C_8$ alkylaromatic hydrocarbon isomer, and having a $C_8$ naphthenes/$C_8$ alkylaromatics weight ratio of below 1:50 and preferably below 1:100. By "substantially equilibrium" is meant at least 90% of the equilibrium concentration. By employing dehydrogenation conditions in the second step of the process to reduce the $C_8$ naphthenes content of the processed hydrocarbon stream to a low level, the amount of molecular hydrogen and the amount of $C_8$ alkylaromatics which are retained in the system after toluene separation are both increased. By decreasing the $C_8$ naphthenes in the final product mixture to a low concentration, it is possible to remove diluent and by-product toluene from the system without losing a substantial amount of naphthenes at the same time. Molecular hydrogen is retained in the system by separating it in a conventional manner from the final hydrocarbon product mixture after the second processing step to allow recycle of the hydrogen to the first and/or second conversion steps. Production of hydrogen in the second step by the dehydrogenation of naphthenes thereby allows hydrogen to be retained in the isomerization-separation system rather than allowing hydrogen to be lost as a component of $C_8$ naphthenes, unavoidably lost with toluene during removal of toluene from the system.

Dehydrogenation conditions employed in the second stage conversion step of the present process includes a temperature at least 25° F higher than the isomerization temperature employed in the first, isomerization stage. Preferably, the dehydrogenation temperature is at least 50° F higher than the isomerization temperature. The hydrogen pressure used in a dehydrogenation step is the same, or lower than, the isomerization pressure. By lowering the pressure in the second step, an effect the same as raising the temperature is observed. A hydrogen/hydrocarbon molar ratio of about 2 to 15 is maintained in the second step. The second step may be performed in a bath-type or continuous-type operation. Preferably, a continuous-type operation is employed using a hydrocarbon liquid hourly space velocity of about 0.5 to 10. Any suitable, conventional reaction vessel may be used in carrying out the dehydrogenation step.

The final hydrocarbon product mixture resulting from the second (dehydrogenation) step of the process is separated from hydrogen. The final product mixture includes a substantially equilibrium concentration of the selected product isomer and has a $C_8$ naphthenes/$C_8$ alkylaromatic weight ratio of less than 1:50. The $C_8$ naphthenes/$C_8$ alkylaromatics weight ratio of the final product mixture is preferably reduced to below 1:100. Reducing the $C_8$ naphthenes content allows more complete separation of a $C_8$ alkylaromatics from diluents and by-products in the product mixture, such as toluene. Removal of toluene is thus made possible without loss of large amounts of $C_8$ naphthenes from the system. Reduction of the $C_8$ naphthenes content is obtained by employing a temperature at least 25° F higher than that used in the isomerization stage, while at the same time maintaining a hydrogen pressure not higher than the hydrogen pressure used in the isomerization stage. The final hydrocarbon product mixture is separated from the process hydrogen stream by conventional means, such as cooling and flash separation of a gaseous, hydrogen-rich phase from a liquid phase containing the final hydrocarbon product mixture. The hydrogen-rich gas thus obtained may conveniently be recycled for further use in the isomerization and dehydrogenation steps of the process.

The final hydrocarbon product mixture is treated to recover the selected isomer, preferably paraxylene and-/or orthoxylene. In a case of paraxylene recovery, the final product mixture is fractionated to provide a $C_8$ alkylaromatics fraction which is relatively free from toluene and hydrocarbons lighter than toluene and free from $C_9$ and heavier hydrocarbons. The lighter and heavier hydrocarbons are removed from the system. Paraxylene is then recovered from the $C_8$ alkylaromatics fraction by separation means such as a crystallization separation system or molecular sieve separation system, in a manner well known to those skilled in the art. In a case of orthoxylene recovery, orthoxylene has a boiling point sufficiently different from ethylbenzene and the other xylene isomers to allow separation of orthoxylene to be made economically by fractionation in a conventional manner.

One preferred method for separating paraxylene is by fractional crystallization of paraxylene from a $C_8$ alkylaromatic fraction. Generally, the $C_8$ alkylaromatic fraction is cooled to a low temperature, e.g., −100° F. The cooling results in crystallization of part of the $C_8$ fraction, with the crystals being rich in paraxylene. The crystals are then separated from the paraxylene-lean mother liquor by, for example, centrifugation. The paraxylene concentration of the crystals that are recovered can be increased by serial crystallization procedures, the use of other solvents, and other known methods. Further details of crystallization procedures may be obtained from U.S. Pat. Nos. 2,985,694 and 3,467,724, the teachings of which are incorporated herein by specific reference.

The raffinate or mother liquor recovered from the paraxylene separation step should be recycled to the first and second processing steps of the process in order to achieve economical recovery of paraxylene. Thus, the feedstocks charged to the isomerization step in the process preferably consist in part of fresh feed and partly consist of recycled $C_8$ alkylaromatics, such as a paraxylene- or orthoxylene-lean raffinate from the separation step of the process.

The present process may be performed in blocked operation using the heaters, reactors and hydrogen circulation equipment of a catalytic naphtha reforming system. Naphtha reforming systems normally include two, three or more reactors in series, one or more of which can be used to provide a suitable isomerization reactor for performing the first stage of the present process, and one or more of which can be used to provide a suitable dehydrogenation reactor for performing the second stage. When the reforming reactors have therein the desired platinum-rhenium-halogen-alumina catalyst, the unit can conveniently be used for alternately reforming a naphtha and isomerizing a $C_8$ alkylaromatic according to the invention. The heaters, located upstream from each of the reforming reactors, can be used to provide the desired higher and lower conversion temperatures required in the first and second steps of the process.

The following Illustrative Embodiment describes a preferred embodiment of the present process. The Embodiment discloses one mode of operation of the process and is not a limitation on the generally broad scope of the invention.

ILLUSTRATIVE EMBODIMENT

In a preferred embodiment of the invention, using a xylene isomerization and recovery system such as that depicted in the attached drawing and described above, an alkylaromatics-containing hydrocarbon stream is passed into the system through the conduit 24 at the rate of 13,400 pounds per hour orthoxylene, 17,760 pounds per hour metaxylene, 11,000 pounds per hour paraxylene, 7,200 pounds per hour ethylbenzene, 2100 pounds per hour toluene and 19,000 pounds per hour of $C_9+$ hydrocarbons.

This alkylaromatics-containing stream is mixed with an alkylaromatic hydrocarbon stream flowing through the conduit 22 at the rate of 16,130 pounds per hour orthoxylene, 37,240 pounds per hour metaxylene, 17,100 pounds per hour paraxylene, 10,300 pounds per hour ethylbenzene, 320 pounds per hour toluene and 700 pounds per hour of $C_8$ naphthenes, and the mixture is passed into the fractionator 23. A bottoms stream containing 22,770 pounds per hour orthoxylene and 20,180 pounds per hour $C_9+$ hydrocarbons is withdrawn from the fractionator 23 and from the processing system via conduit 25. The overhead from fractionator 23 passes through conduit 26 into the crystallization separation zone 27 at the rate of 6,760 pounds per hour orthoxylene, 55,000 pounds per hour metaxylene, 28,100 pounds per hour paraxylene, 17,500 pounds per hour ethylbenzene, 2,100 pounds per hour toluene, and 700 pounds per hour $C_8$ naphthenes. Paraxylene is recovered via the conduit 28 at the rate of 19,300 pounds per hour paraxylene and is withdrawn from the system for any desired use. The resulting paraxylene-lens raffinate is withdrawn from the separation zone 27 through the conduit 1 at the rate of 6,740 pounds per hour orthoxylene, 55,000 pounds per hour metaxylene, 8,800 pounds per hour paraxylene, 17,500 pounds per hour ethylbenzene, 700 pounds per hour $C_8$ naphthenes, and 2,100 pounds per hour toluene. Hydrogen-rich gas is introduced into the conduit 1 from the conduit 15 at the rate of two million SCF per hour, and the hydrogen-hydrocarbon mixture is passed into the heater 2 and heated to a temperature of about 800° F. The mixture is then passed through the conduit 3 into the isomerization-hydrogenation reactor 4, which contains a fixed bed of an isomerization catalyst containing 0.3 wt% platinum, 0.3 wt% rhenium and 1.6 wt% chloride on a particulate alumina carrier. The hydrogen-hydrocarbon mixture is passed in downflow fashion through the catalyst bed at an LHSV of 2 and a hydrogen pressure of 230 psig. The resulting intermediate reaction mixture is removed from the reactor 4 through conduit 5 at the rate of 15,570 pounds per hour orthoxylene, 36,160 pounds per hour metaxylene, 16,600 pounds per hour paraxylene, 10,040 pounds per hour ethylbenzene, 3,900 pounds per hour $C_8$ naphthenes, 700 pounds per hour benzene, 4,800 pounds per hour toluene, 550 pounds per hour heavier hydrocarbons and some lighter hydrocarbons. The intermediate reaction mixture is passed into the heater 6, wherein it is heated to a temperature of about 850° F. The mixture is then passed through the conduit 7 into the dehydrogenation reactor 8, which contains a fixed bed of isomerization-dehydrogenation catalyst containing 0.3 wt% platinum, 0.3 wt% rhenium and 1.6 wt% chloride on a particulate alumina carrier. The intermediate reaction mixture is passed in downflow fashion through the catalyst bed at a hydrogen pressure of 230 psig and an LHSV of 2. The resulting final hydrocarbon product mixture is removed from the reactor 8 through the conduit 9 at the rate of 16,130 pounds per hour orthoxylene, 37,470 pounds per hour metaxylene, 17,200 pounds per hour paraxylene, 10,400 pounds per hour ethylbenzene, 1,180 pounds per hour $C_8$ naphthenes, 700 pounds per hour benzene, 5,340 pounds per hour toluene, 300 pounds per hour of lighter hydrocarbons and 1,180 pounds per hour of $C_9+$ hydrocarbons. The final mixture is cooled in the cooler 10 to a temperature of about 100° F and passed through the conduit 11 into the vapor-liquid separator vessel 12 at a pressure of about 170 psig. Hydrogen-rich gas is removed from the vessel 12 through the conduit 13, and any necessary makeup hydrogen is introduced into the conduit 13 by way of the conduit 29. The recycle and makeup hydrogen is pressurized to about 230 psig in the compressor 14 and recycled through the conduit 15 to the conduit 1 for further use as described above. The liquid hydrocarbons are withdrawn from the vessel 12 and passed through the conduit 16 to the fractionator 17. Light hydrocarbons in the $C_1-C_4$ boiling range are separated and removed overhead from the fractionator 17 through the conduit 18 at the rate of 300 pounds per hour. Heavier hydrocarbons are removed as bottoms via the conduit 19 and are passed into the fractionator 20. In the fractionator 20, benzene, toluene and like boiling range hydrocarbons are separated and removed overhead through the conduit 21 at the rate of 480 pounds per hour of $C_8$ naphthenes, 5,020 pounds per hour toluene, 1,580 pounds per hour benzene, 230 pounds per hour metaxylene, 100 pounds per hour paraxylene and 100 pounds per hour ethylbenzene. Heavier hydrocarbons are removed as bottoms via the conduit 22.

What is claimed is:

1. A process for producing a first selected xylene isomer from a feedstock including a substantially greater than equilibrium concentration of ethylbenzene, a substantially less than equilibrium concentration of said selected isomer, and a weight ratio of $C_8$ naphthenes to $C_8$ alkylaromatics of less than 1:50, comprising the steps of:

a. forming an intermediate reaction mixture having a weight ratio of $C_8$ naphthenes to $C_8$ alkylaromatics of greater than 1:50 and less than 1:10 by contacting said feedstock and hydrogen with a first catalyst comprising 0.1-3 weight percent platinum, 0.1-3 weight percent rhenium and 1.25-2.0 weight percent chloride on an alumina carrier at isomerization conditions including an isomerization temperature between about 750° F and 900° F and an isomerization hydrogen pressure of about 100 psia to 250 psia;

b. forming a final hydrocarbon product mixture including a substantially equilibrium concentration of said first isomer and having a weight ratio of $C_8$ naphthenes to $C_8$ alkylaromatics of less than 1:50 by contacting said intermediate reaction mixture with a second catalyst having essentially the same composition as said first catalyst and comprising 0.1-3 weight percent platinum, 0.1-3 weight percent rhenium, and 1.25-2.0 weight percent chloride on an alumina carrier at dehydrogenation conditions including a temperature at least 25° F above said isomerization hydrogen temperature and in the range from about 775° F to 950° F and a pressure not higher than said isomerization hydrogen pressure; and c. recovering said first isomer from said final product mixture.

2. A process according to claim 1 wherein said selected xylene isomer is paraxylene.

3. A process according to claim 1 wherein the weight ratio of $C_8$ naphthenes to $C_8$ alkylaromatics in said intermediate reaction mixture is between 1:33 and 1:20.

* * * * *